United States Patent [19]

Jones et al.

[11] Patent Number: 4,803,210

[45] Date of Patent: Feb. 7, 1989

[54] CARDIOTONIC TRICYCLIC OXAZOLONES

[75] Inventors: Winton D. Jones; Richard A. Schnettler; George P. Claxton; Richard C. Dage, all of Cincinnati, Ohio

[73] Assignee: Merrell Dow Pharmaceuticals Inc., Cincinnati, Ohio

[21] Appl. No.: 183,537

[22] Filed: Apr. 14, 1988

Related U.S. Application Data

[63] Continuation of Ser. No. 55,485, May 29, 1987, abandoned.

[51] Int. Cl.$^4$ .................... A61K 31/42; C07D 498/04
[52] U.S. Cl. ........................................ 514/293; 546/83
[58] Field of Search ........................... 546/83; 514/293

[56] References Cited

U.S. PATENT DOCUMENTS

| | | | |
|---|---|---|---|
| 4,532,250 | 7/1985 | Stout et al. | 546/144 |
| 4,668,683 | 5/1987 | Takai et al. | 544/293 |
| 4,668,686 | 5/1987 | Meanwell et al. | 546/82 |
| 4,670,451 | 6/1987 | Uematsu et al. | 548/221 |

FOREIGN PATENT DOCUMENTS

2056224  6/1971  Fed. Rep. of Germany ........ 546/84

*Primary Examiner*—Mary C. Lee
*Assistant Examiner*—J. Richter
*Attorney, Agent, or Firm*—Stephen L. Nesbitt; Alice A. Brewer

[57] ABSTRACT

Tricyclic oxazolones enhance myocardial contractile force and are useful as cardiotonics in the treatment of heart failure.

16 Claims, No Drawings

CARDIOTONIC TRICYCLIC OXAZOLONES

CROSS-REFERENCE TO RELATED APPLICATION

This is a continuation of U.S. application Ser. No. 55,485, filed May 29, 1987 and now abandoned.

BACKGROUND OF THE INVENTION

This invention relates to the use of certain tricyclic oxazolones to enhance myocardial contractile force. These compounds are useful as cardiotonics in the treatment of heart failure.

Heart failure is that physiological condition resulting from the inability of the ventricular myocardium to maintain adequate blood flow to the peripheral body tissues and includes congestive heart failure, backward and forward heart failure, right ventricular and left ventricular heart failure, and low-output heart failure. Heart failure can be caused by myocardial ischemia, myocardial infarction, excessive alcohol usage, pulmonary embolism, infection, anemia, arrhythmias, and systemic hypertension. Symptoms include tachycardia, fatigue with exertion, dyspnea, orthopnea, and pulmonary edema.

Treatment involves either removal or correction of the underlying causes or involves control of the heart failure state. Management or control can be accomplished by increasing cardiac output or by decreasing cardiac workload. While workload can be accomplished by reduction of physical activities and physical and emotional rest, increasing cardiac output has traditionally involved digitalis therapy. Digitalis stimulates contractile force of the heart which increases cardiac output and improves ventricular emptying. In this way digitalis therapy normalizes venous pressure and reduces peripheral vasoconstriction, circulatory congestion, and organ hypoperfusion.

Unfortunately, optimal doses of digitalis vary with the patient's age, size, and condition and the therapeutic to toxic ratio is quite narrow. In most patients the lethal dose is only about five to ten times the minimal effective dose with toxic effects becoming apparent at only 1.5 to 2.0 times the effective dose. For these reasons, dose must be carefully tailored to suit the individual and frequent clinical examinations and electrocardiogram is necessary to detect early signs of digitalis intoxication. Despite this care digitalis intoxication is reported in up to one-fifth of hospitalized patients undergoing therapy.

The need for less toxic and more effective cardiotonic agents is readily apparent. Applicants have discovered certain tricyclic oxazolones which possess potent cardiotonic and vasodilation activity and by comparison to digitalis have few toxic effects.

SUMMARY OF THE INVENTION

This invention relates to certain oxazolones of structure 1:

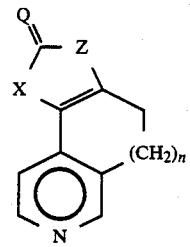

wherein
Q is a divalent sulfur or oxygen atom;
one of X and Z is an oxygen atom and the other is an imino (NH) group; and
n is 0 or the integer 1 or 2 and the pharmaceutically acceptably salts thereof as well as the use of these compounds as vasodilators, to enhance myocardial contractile force, and to treat heart failure, their pharmaceutical compositions, and the process of their preparation.

DETAILED DESCRIPTION OF THE INVENTION

The oxazole ring of the compounds of structure 1 exist in several tautomeric forms. Throughout this disclosure, the tricyclic oxazolones of structure 1 are intended to include these tautomers as well.

The ring nitrogen atom of the oxazole ring in the structure 1 compounds can be substituted with a ($C_1$–$C_5$) alkyl group, an alkanoyl group such as an acetyl group, or benzoyl group. These nitrogen substituted compounds are equivalent to the unsubstituted compounds primarily because the substitutent is cleaved upon administration to a patient and also because many of the nitrogen substituted compounds independently possess significant ability to enhance myocardial contractile force and are useful cardiotonic agents.

As is true for most classes of therapeutically effective compounds, certain subclasses and certain species are more effective than others. In this instance those compounds of structure 1 wherein Q is a divalent oxygen atom are preferred. Also preferred are those compounds wherein n is the integer 1 or 2 and those compounds wherein X is an oxygen atom and Z is an imino group. More preferred are those compounds of structure 1 wherein Q is a divalent oxygen atom, n is the integer 1 or 2, X is an oxygen atom, and Z is an imino group.

The compounds of this invention are useful both in the free base form and in the form of acid addition salts. The acid addition salts are simply a more convenient form for use and, in practice, use of the salt amounts to use of the free base. The expression "pharmaceutically acceptable acid addition salts" is intended to apply to any non-toxic organic or inorganic acid addition salts of the base compounds of formula 1. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative of such acids are, for example, the sulfonic acids such as methane sulfonic acid and 2-hydroxyethane sulfonic acid. Either the mono- or the diacid salts can be formed, and such salts can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution.

The compounds of structure 1 wherein X is a oxygen atom and Z is an imino group can be readily prepared by the heat activated decomposition of the condensation product of a cyclic alpha amino ketone of structure 2 with N,N'-carbonyldiimidazole (CDI) as illustrated in scheme 1: The condensation reaction is performed by allowing the structure 2 compound to react with CDI, preferably a 2 to 5 fold molar excess, of CDI in water. Preferably the temperature of this reaction is maintained below 10° C., conveniently at about 0° C. After about 10 to 20 minutes, the crude condensation product is isolated, for example, by extraction of the reaction mixture with ethyl acetate, and subsequent removal of the ethyl acetate by evaporation. The isolated crude condensation product is then heated, preferably at from about 150° to about 200°, more preferably at about 170° C., at reduced pressure for from 5 to about 30 minutes and the product isolated.

The compounds of structure 1 wherein Q is a divalent sulfur atom are prepared from the corresponding compounds of structure 1 wherein Q is a divalent oxygen atom in the ususal manner by treatment with Lawesson's Reagent, see M. P. Cava. and M. I. Levinson, *Tetrahedron* 41, 5061 (1985).

Scheme 1

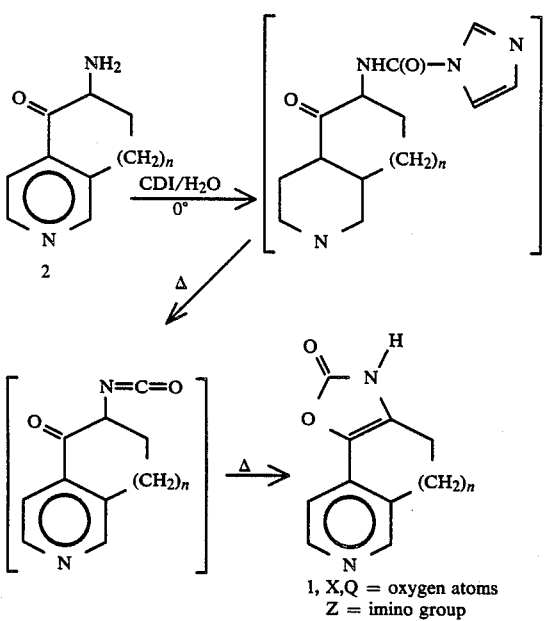

The cyclic alpha amino ketones of structure 2 are prepared from the corresponding cyclic ketone of structure 3 via the oxime of structure 3A and the para toluene sulfonyl, tosyl (Ts), derivative of structure 3B as illustrated in Scheme 2.

The oxime of structure 3A is readily prepared from the cyclic ketone of structure 3 by any method known to be useful for this conversion, for example, by reacting the cyclic ketone with hydroxylamine. The oxime derivative is then converted to the tosyl derivative of structure 3B by any standard technique such as by reaction with tosyl chloride in the presence of a proton acceptor such as triethylamine. The structure 3B tosyl derivative is then converted to the cyclic oxime utilizing the Neber rearrangement, a well known means of converting ketoximes to alpha amino ketones and is discused in, for example, March, Advanced Organic Chemistry: Reactions, Mechanisms, and Structure, McGraw-Hill Book Company, New York, 1968, page 815–16, and is reviewed in C. O'Brien, *Chem. Revs.* 64, 81 (1964); D. J. Cram, Fundenmentals of Carbanion Chemistry (Academic Press, New York, 1965), p. 249; C. G. McCarty in S. Patai, Ed., Chemistry of the Carbon-Nitrogen Double Bond (Interscience, New York, 1970) p. 4471; T. S. Stevens, W. E. Watts, Selected Rearrangements 1973, p. 138; Y. Tamura et al., *Synthesis* 1973, 215; and R. F. Parcell, J. C. Sanchez, *J. Org Chem.* 46, 5229 (1981).

Scheme 2

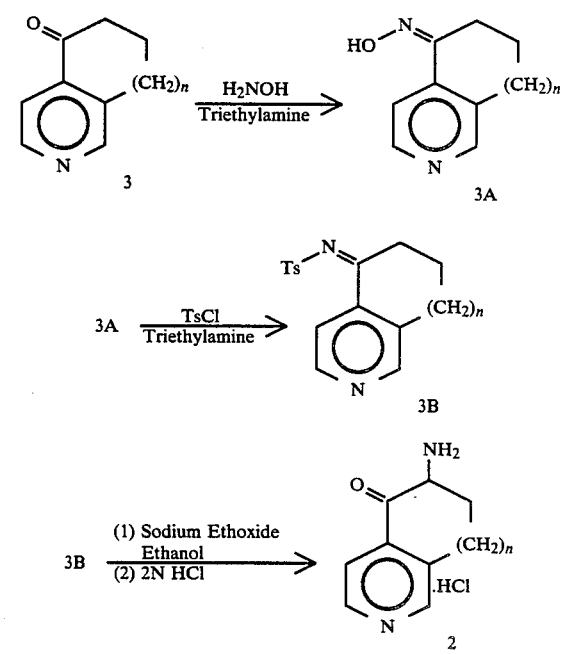

The compound of structure 3 wherein n is the integer 1 is known from J. Epsztain and A. Bieniek, *J. Chem. Soc. Perkin Trans.* 1, 213 (1985). This compound and the compounds wherein n is zero or the integer 2 can be prepared from the corresponding compound of structure 4 via the N-oxide derivative of structure 4A, the acetate (AcO) derivative of structure 4B, and the alcohol derivative of structure 4C as illustrated in Scheme 3.

The N-oxide derivatives are easily preared by any means generally by those skilled in the art such as by treating a compound of structure 4 with hydrogen peroxide in acetic or formic acid. The acetate derivatives are then readily prepared by heating the N-oxide, preferably to the reflux temperature, as for example, a mixture of the corresponding N-oxide derivative of structure 4A and acetic anhydride. The acetate derivative is then converted into the alcohol by simple ester hydrolysis, for example, by heating a solution of the acetate in dilute aqueous acid such as dilute hydrochloric acid (5 N). The cyclic ketones of structure 3 are then prepared from the corresponding alcohol of structure 4 by oxidation utilizing any effective means genreally known to those skilled in the art taking into consideration that the oxidizing agent must not oxidize other funtionalities in the molecule such as the amine nitrogen. Applicants have oxidized the alcohols of structure 4 by treatment with a mixture of oxalyl chloride and dimethylsulfoxide followed by addition of a proton acceptor such as triethylamine.

Scheme 3

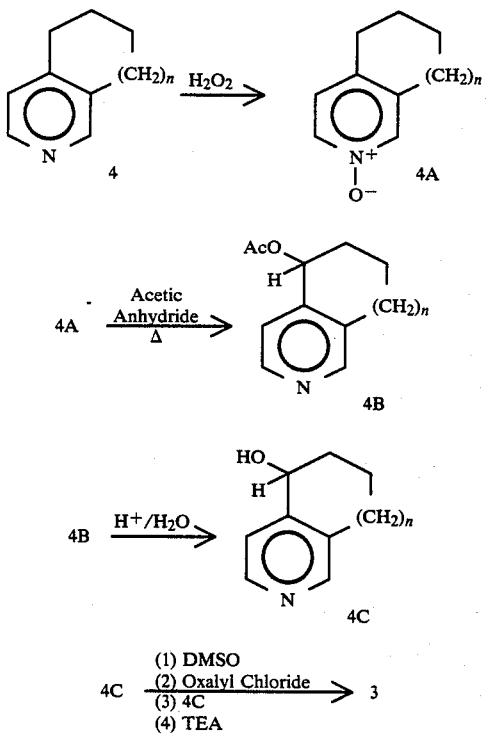

The compound of structure 4 wherein n is the integer 1 is prepared by the catalytic reduction of isoquinoline using, for example, a palladium on carbon catalyst. The compounds of structure 4 wherein n is zero or the integer 2 are formed from the product of the 2 +4, Diels-Alder like, addition reaction of 1,2,4-triazine with the enamine of cyclopentanone or cycloheptanone with pyrrolidine as illustrated in scheme 4 and described by D. L. Boger, et al., *J. Org. Chem.* 47, 895 (1982). The formation of the enamine is facilitated by a dehydrating agent such as 4A molecular seives. The product of the 2 +4 addition reaction upon spontaneous loss of pyrrolidine and molecular nitrogen yields the desired product of structure 4. The compound 1,2,4-triazine is known from W. W. Pandler and T. K. Chen, *J. Heterocylic Chem.* 767 (1970).

Scheme 4

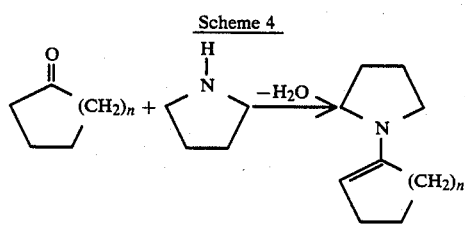

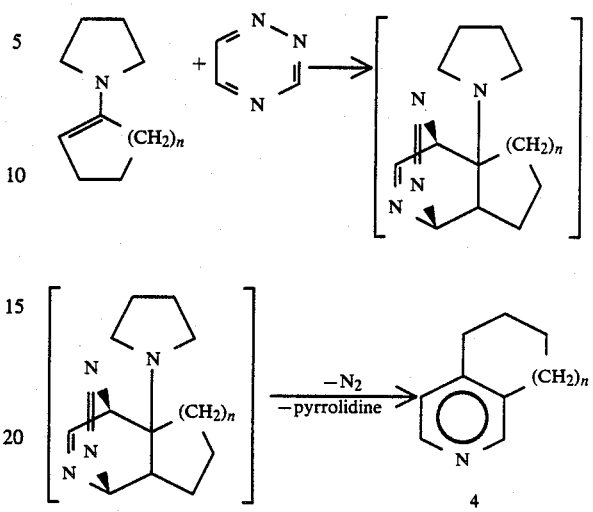

The compounds of structure 1 wherein X is an imino group and Z is an oxygen atom can be readily prepared in a manner analogous to the preparation of those compounds of structure 1 wherein X is an oxygen atom and Z is an imino group by the heat activated decomposition of the condensation product of a cyclic alpha amino ketone of structure 2' with N,N'-carbonyldiimidazole (CDI) as illustrated in scheme 5:

Scheme 5

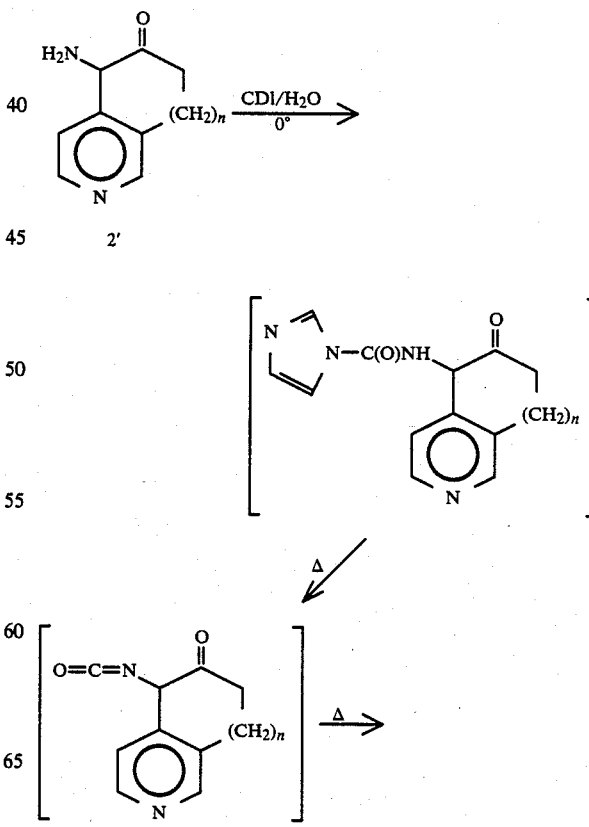

Scheme 5 -continued

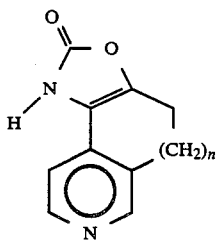

1, X = imino group
Z, Q = oxygen atoms

The compounds of structure 2, are in turn prepared from the ketones of structure 3, via the hydroxyimino derivative of structure 5 as illustrated in scheme 6.

Scheme 6

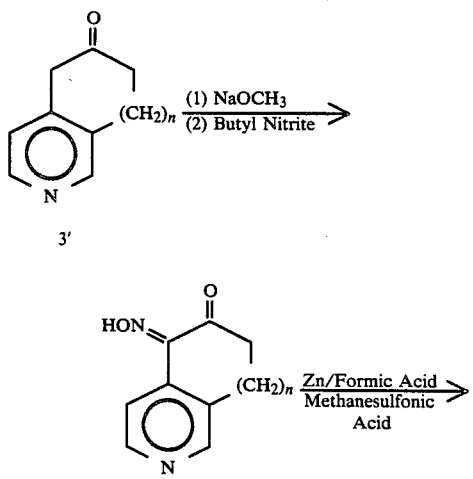

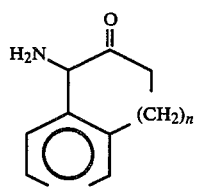

The ketone is converted to the hydroxyimino derivative utilizing any conventional means, for example, the ketone of structure 3 can be treated with a base such as sodium methoxide to form the enolate anion which upon subsequent addition of butyl nitrite results in formation of the desired hyroxyimino derivative. Reduction of the hydroxyimino derivative can be accomplished using a variety of well known techniques such as by treatment with zinc powder in formic acid.

The ketones of structure 3' can be prepared either by a 1,2 carbonyl transposition of an appropriate ketone of structure 3 as illustrated in scheme 7 or from the methyl ketones of structure 6 as illustrated in scheme 8. Carbonyl transpositions are well known and the preparation of the structure 3 ketones is outlined above. The structure 6 methyl ketone is transformed into the enamine of structure 6A with pyrrolidine in any conventional manner. The formation of the enamine is facilitated by the presence of a dehydrating agent such as 4A molecular seives. The structure 6A enamine then undergoes a 2+4, Diels Alder like, addition with 1,2,4-triazine, see W. W. Pandler and T. K. Chen, *J. Heterocyclic Chem.* 767 (1970), and the addition product spontaneously losses pyrrolidine and molecular nitrogen upon heating to form the desired methyl pyridone derivative of structure 6B.

Scheme 7

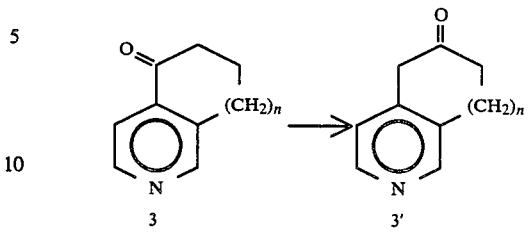

Scheme 8

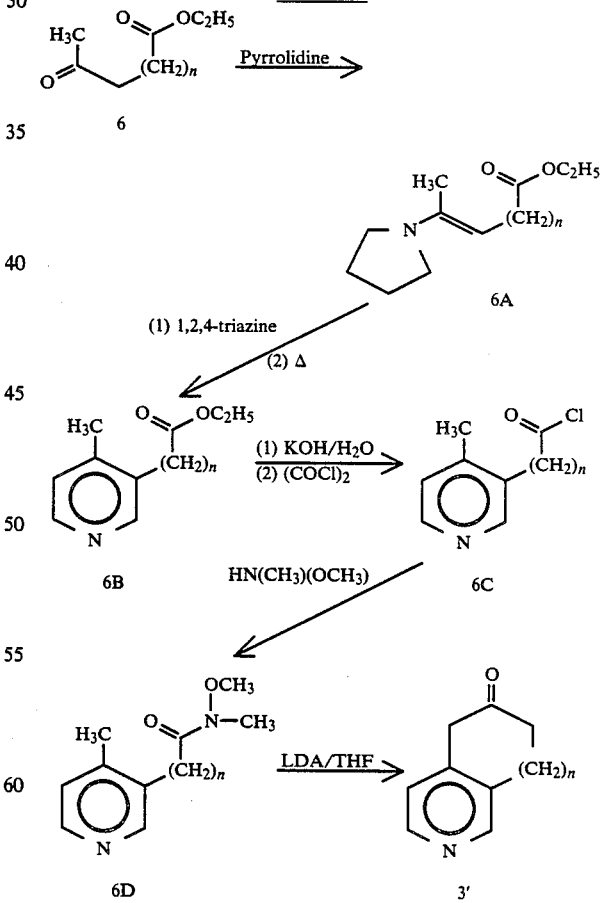

Upon hydrolysis of the ester moiety of the structure 6B compound with, for example, aqueous potassium hydroxide, the carboxylate can react with oxalyl chloride, $(COCl)_2$, to form the corresponding acid chloride of structure 6C. Treatment of the acid chloride with O-methyl, methyl hydroxylamine, $HN(CH3)(OCH3)$, results in the amide of structure 6D, which upon low temperature lithiation with lithium diisopropylamide (LDA) cyclizes to form the desired ketone of structure 3'.

The compounds of structure 1 are cardiotonic agents useful in the treatment of heart failure and are believed to function by strengthening the heart muscle by virtue of their ability to enhance myocardial contractile force and reducing work load by virtue of their vasodilator activity. The utility of the structure 1 compounds as cardiotonic agents may be determined by administering the test compound (0.1-100 mg/kg) intraveneously, intraperitoneally, intraduodenally, or intragastrically in a suitable vehicle to a mongrel dog (either sex). The test dogs are anesthetized and prepared by isolating a suitable artery (e.g., femoral or common carotid) and vein (e.g., femoral or external jugular) and introducing polyethylene catheters filled with 0.1% Heparin-Sodium to record arterial blood pressure and administer compounds, respectively. The chest is opened by splitting the sterum at the midline or by an incision at the left fifth intercostal space, and a pericardial cradle is formed to support the heart. A Walton-Brodie strain gage is sutured to the right or left ventricle to monitor myocardial contractile force. An electromagnetic flow probe may be placed around the root of the ascending aorta for measuring cardiac output less coronary blood flow. A catheter may also be put into the left atrium or the left ventricle of the heart to record left atrial pressure or left ventricular pressure. Heart failure is induced by administering sodium pentobarbital (20 to 40 mg/kg) followed by a continuous infusion of 0.25-2 mg/kg/min. or propranolol hydrochloride (4 mg/kg) followed by a continuous infusion of 0.18 mg/kg/min. to the blood perfusing the heart. Following administration of either of the cardiac depressants, the right atrial pressure dramatically increases and cardiac output is severly depressed. Reversal of these effects by the test compound indicates cardiotonic activity.

The amount of the active ingredient to be administered can vary widely according to the particular dosage unit employed, the period of treatment, the age and sex of the patient treated, and the nature and extent of the disorder treated. The total amount of the active ingredient to be administered will generally range from about 0.1 mg/kg to 100 mg/kg and preferably from 0.3 mg/kg to 20 mg/kg. A unit dosage may contain from 25 to 500 mg of active ingredient, and can be taken one or more times per day. The active compound of formula 1 can be administered with a pharmaceutical carrier using conventional dosage unit forms either orally, parenterally, or topically.

As used herein, the term "patient" is taken to mean warm blooded animals, for example, birds such as chickens and turkeys, and mammals such as sheep, horses, cattle, pigs, dogs, cats, rats, mice, and primates including humans.

The preferred route of administration is oral administration. For oral administration the compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The active ingredient may also be administered by means of a sustained release system whereby the compound of formula 1 is gradually released at a controlled, uniform rate form an inert or bioerodible carrier by means of diffusion, osmosis, or disintegration of the carrier during the treatment period. Controlled release drug delivery systems may be in the form of a patch or bandage applied to the skin or to the buccal, sublingual, or intranasal membranes, or a gradually eroding tablet or capsule or a gastrointestinal reservoir administered orally. Administration by means of such sustained release delivery systems permits the tissues of the body to be exposed constantly for a prolonged time period to a therapeutically or prophylactically effective dosage of a compound of formula 1. The unit dosage of the compound administered by means of a sustained release system will approximate the amount of an effective daily dosage multiplied by the maximum number of days during which the carrier is to remain on or in the body of the host. The sustained release carrier may be in the form of a solid or porous matrix or reservoir and may be formed from one or more natural or synthetic polymers, including modified or unmodified cellulose, starch, gelatin, collagen, rubber, polyolefins, polyamides, polyacrylates, polyalcohols, polyethers, polyesters, polyurethanes, polysulphones, polysiloxanes, and polyimides as wells as mixtures and copolymers of these polymers. The compounds of formula 1 may be incorporated in the sustained release carrier in a pure form or may be dissolved in any suitable liquid or solid vehicle, including the polymer of which the sustained release carrier is formed.

EXAMPLES

The following specific examples illustrate the preparation of the compounds of this invention as well as the pharmaceutical compositions containing these compounds but are not intended to limit the scope of the invention.

EXAMPLE 1

Preparation of
4,5-dihydrooxazolo[5,4-f]isoquinolin-2(3H)-one

A. Preparation of 5-hydroxyiminoisoquinoline (Structure 3A: n=1)

Isoquinolin-5-one (21.57g, 0.147M) and hydroxylamine (15.55g, 0.22M) together with approximately 300 ml of dry ethanol and 75 ml of pyridine were stirred at reflux temperature of the mixture for 6 hours. The solvent was then removed by evaporation and the residue was dissolved in a mixture of diethyl ether and water (600 ml, ca. 1:1). The organic phase was separated and extracted with water to remove residual pyridine, washed with saturated, aqueous solution of sodium chloride and dried over magnesium sulfate crystals. The inorganic matter was removed by filtration and the solvent by evaporation leaving 14.7 grams of the desired product (61.7% yield).

B. Preparation of the tosyl ester of 5-hydroxyiminoisoquinoline (Structure 3B: n=1)

Tosyl chloride (20.7 g, 0.109 M) was added portionwise over five minutes to a solution of 5-hydroxyiminoisoquinoline (14.7g, 0.0906 M) in dry pyridine (ca 200 ml) at 0° C. The mixture was then stirred at ~0° C. for 2 hours after addition was complete, cooled at about 4° C. for 48 hours, and finally quenched with about 1200 ml of water. The solid product was collected by filtration and dried (75.9%), m.p. 125°–127° C. (dec.).

C. Preparation of 6-aminoisoquinolin-5-one (Structure 2: n=1)

Spherical sodium (2.37 g, 0.103 M) was aded to dry ethanol (50 ml) and stirred until the sodium had completely dissolved. A mixture of the tosyl ester of 5-hydroxyiminoisoquinoline (0.0687M) and ethanol (350 ml) was added over a 5 minute period then allowed to react at room temperature for ~2½ hours and subsequently at ~4° C. overnight. The mixture was added to diethyl ether (ca. 2½ l) then filtered to remove the precipitate. The filtrate was extracted with hydrochloric acid (~400 ml, 2N HCl) and the solvent removed by evaporation to yield the desired product (70.0%).

D. Preparation of 4,5-dihydrooxazolo[5,4-f]isoquinolin-2(3H)-one (Structure 1: X=O, Z=NH, n=1)

N,N'-carbonyldiimidazole (16 g) was added to a solution of 6-aminoisoquinolin-5-one (6.0 g,0.0255 M) in water (75ml) at 0° C. over a 5–10 minute period. After stirring for about 15 minutes, the mixture was extracted with ethyl acetate (400 ml). The extract was washed with an aqueous, saturated solution of sodium chloride and dried over crystals of magnesium sulfate. After filtering to remove the solid inorganic matter, the solvent was removed by evaporation and the residue heated at 170° C. in vacuo for 10 to 15 minutes, allowed to cool, then extracted with water to remove any liberated imidazole. The aqueous phase was removed by decantation to yield the desired product, m.p. 290°–292° C. Analysis calculated for: $C_{10}H_8N_2O_2$: C, 63.82; H, 4.28; N, 14.89. Found: C, 63.68; H, 4.32; N, 14.68.

EXAMPLE 2

Preparation of
3,4,5,6-tetrahydro-2H-oxazolo[5',4':3,4]cyclohepta[1,2-c]pyridin-2-one A. Preparation of cyclohepta[1,2-c]pyridine, N-oxide (Structure 4A: n=2)

Hydrogen peroxide (30 ml, 30%) was added to a stirred mixture of cyclohepta[1,2-c]pyridine (28.40 g, 0.193 mole) and acetic acid (120 ml) at room temperature. After the addition was complete, the reaction mixture was heated with stirring at 70°–80° C. for 11 hr, after which additional hydrogen peroxide (30 ml, 30%) was added and the mixture stirred for another 12 hours with heating and for 48 hours at room temperature. The pale yellow reaction mixture (~200 ml) was concentrated to 75 m on the rotary evaporator, then diluted with 100 ml of $H_2O$ and concentrated to ~50 ml on the rotary evaporator. The pale yellow liquid was diluted with methylene chloride (300 ml), then neutralized with solid potassium carbonate (pH ~8), then filtered through celite. The filtrate was poured into a separatory funnel and the organic layer removed and washed with brine, dried, and filtered. Concentration of the filtrate gave 26.75g (85%) of a pale yellow solid. The solid was washed with hexane, then collected on a buchner funnel to give 24.72 g of the desired product as a light tan solid.

B. Preparation of 5-acetyloxycyclohepta[1,2-c]pyridine (Structure 4B: n=2)

Cyclohepta[1,2-c]pyridine, N-oxide (24.00 g, 0.147 mole) was added portionwise to a stirred solution of acetic anhydride (140 ml). The resulting yellow mixture was then stirred for 2 hours at its reflux temperature and overnight at room temperature. Excess acetic anhydride was removed by evaporation at ~55° C. on a rotary evaporator and the dark brown, oily residue was distilled (170°, 0.03 mm) and chromatographed on silica gel eluting with a mixture of ethyl acetate in methylene chloride (1:4) to give the desired product.

C. Preparation of 5-hydroxycyclohepta[1,2-c]pyridine (Structure 4C: n=2)

A solution of 5-acetyloxycyclohepta[1,2-c]pyridine in hydrochloric acid (75 ml, ca. 5 N) was heated and stirred at its reflux temperature for 6½ hrs. The resulting red-colored solution was stirred overnight, then neutralized with solid $K_2CO_3$ (pH=8) and the oily precipitate extracted with methylene chloride. The organic phase was separated, washed with brine, and dried ($MgSO_4$). Filtration through celite gave a light yellow filtrate which on concentration gave a gummy brown solid. The solid was triturated with hexane and collected by filtration. The yield of light tan solid was 5.10 g (59%), m.p. 127°-129° C.

Calculated for $C_{10}H_{13}NO$: C, 73.59; H, 8.03; N, 8.58. Found: C, 73.32; H, 8.04; N, 8.52; and C, 73.28; H, 8.20; N, 8.70.

D. Preparation of cyclohepta[1,2-c]pyridin-5-one (Structure 3: n=2)

Dimethylsulfoxide (9.37 g, 0.12 mole) was added dropwise to a stirred solution of oxalyl chloride (7.61 g, 0.060 mole) in methylene chloride (120 ml) maintained at betweeen −70° C. to −60° C. The mixture was stirred for 10 minutes at -70° C., then a solution of 5-hydroxycyclohepta[1,2-c]pyridine (10.00 g, 0.061 mole) and additional dimethylsulfoxide (12 ml) in methylene chloride (~115 ml) was added rapidly (~10 minutes) while maintaining the temperature of the reaction mixture at −70° C. After stirring for an additional 30 minutes at −75° C. to 60° C., a solid precipitate was present. Triethylamine (37.026 g, 0.366 mole) was added rapidly at −70° C. and the resulting yellow reaction mixture was stirred at −70° C. for ~10 minutes, then allowed to warm to room temperature. After about 48 hours at room temperature the reaction mixture was quenched with water (600 ml), the organic phase separated, then extracted with water (2X, 500 ml), aqueous sodium bicarbonate (5%, 2X, 500 ml), and brine. After drying, the organic layer was filtered through celite and concentrated by solvent evaporation to give 9.00 g of a brown oil. Distillation (90°-120° C., 0.03 mm) gave the desired product as a yellow liquid (07.41 g, 75%). The analytical sample was prepared by chromatography of ~0.1 g on a 20×20 cm preparative tlc plate eluting with a mixture of 35% ethanol - 65% methylene chloride.

Calculated for: $C_{10}N_{11}NO$ (163.20); C, 74,50; H, 6.88; N, 8.69. Found: C, 74.53; H, 7.08; N, 8.65.

E. Preparation of 5-hydroxyiminocyclohepta[1,2-c]pyridine (Structure 3A: n=2)

Hydroxylamine hydrochloride (2.20 g, 0.317 mole) was added to a stirred mixture of cyclohepta[1,2-c]pyridin5-one and triethylamine (15.00 ml) and the resulting yellow solution was stirred overnight at its reflux temperature. The pale yellow solution was cooled to room temperature, then concentrated by solvent evaporation to a pasty yellow solid. The solid was dissolved in a mixture of water and diethyl ether (1:1, ~700ml) and the yellow $Et_2O$ layer was separated and extracted with water (2X, 500 ml), washed with brine, then dried ($MgSO_4$). Filtration through celite followed by concentration of the filtrate gave 2.30g (53%) of a yellow solid, which after trituration with hexane and recrystallization from aqueous ethanol, gave the desired product, m.p. 164°-167° C.

Calculated for: $C_{10}H_{12}N_2O$ (176.22), C, 68.15; H, 6.87; N, 15.9. Found: C, 68.42; H, 7.00; N, 15.97.

F. Preparation of the tosyl ester of 5-hydroxyiminocyclohepta[1,2-c]pyridine (Structure 3B: n=2)

Tosyl chloride (3.03 g, 0.0159 mole) was added portionwise to a stirred solution of 5-hydroxyiminocyclohepta[1,2-c]pyridine (2.80 g, 0.0159 mole) and triethylamine (10.89 g, 0.107 mole) in dry methylene chloride maintained at −2° C. The reaction was allowed to proceed for about 12 hours at about 0° C. and the resulting brown mixture was quenched with water (500 ml), The organic phase was extracted with water (2X 500 ml), washed with brine, and dried ($MgSO_4$). Filtration through celite followed by concentration of the filtrate and vacuum drying, gave the desired product, 5.00 g.

G. Preparation of 6-aminocyclohepta[1,2-c]pyridin-5-one (Structure 2: n=2)

A solution of the tosyl ester of 5-hydroxyiminocyclohepta[1,2-c]pyridine (5.00 g, 0.151 mole) in ethanol (50 ml) was added to an ethanolic solution of sodium ethoxide prepared by the reaction of sodium metal (0.76 g) and ethanol (75 ml). After stirring at room temperature for about 1-3/4 hours, and at about 0° C. for about 12 hours, the mixture was poured into diethyl ether (500 ml), filtered, and extracted with hydrochloric acid (2N, 2X 50 ml). The aqueous layer was extracted with diethyl ether (200 ml) and the desired product, 4.20 g, was isolated from the aqueous phase by solvent evaporation.

H. Preparation of 3,4,5,6-tetrahydro-2H-oxazolo[5',4':3,4]cyclohepta[1,2-c]pyridin-2-one (Structure 1: X=O, Z=NH, n=2)

N,N'-carbonyldiimidazole (4.86 g, 0.030 mole) was added portionwise to a stirred, aqueous solution of 6-aminocyclohepta[1,2-c]pyridin-5-one (4.20g, 0.0169 mole) maintained at 2° C. After stirring for 30 minutes, ethyl acetate (~300 ml) was added and the mixture stirred until it reached room temperature. The organic phase was extracted with water (150 ml), washed with brine, and dried ($MgSO_4$). The light brown solid isolated after solvent removal was heated (180° C.) for 35 minutes, cooled to room temperature, then quenched with water (200 ml). The aqueous mixture was stirred for about 12 hours and the brown residue collected by filtration, after washing with ethyl acetate (50 ml), then methylene chloride (50 ml), was recrystallized from aqueous ethanol (50%, ~50 ml) to give 0.29 g of the desired product, m.p. >285° C.

Calculated for: $C_{11}H_{10}N_2O_2$(202.21): C, 65.33: H, 4.98 N, 13.86. Found: C, 65.19: H, 4.99: N, 13.75.

EXAMPLE 3

Tablets are prepared each having the composition:

3,4,5,6-tetrahydro-2H-oxazolo[5',4':3,4]cyclohepta[1,2-c]-pyridin-2-one—250 mg
starch—40 mg
talc—10 mg
magnesium stearate—10 mg

EXAMPLE 4

Capsules are prepared each having the composition:
4,5-dihydrooxazolo[5,4-f]isoquinolin-2(3H)-one—400 mg
talc—40 mg
sodium carboxymethylcellulose—40 mg
starch—120 mg

We claim:

1. A compound of the structure:

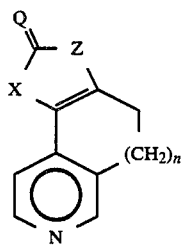

wherein Q is a divalent sulfur or oxygen atom; one of X and Z is an oxygen atom and the other is an imino (NH) group; and n is 0 or the integer 1 or 2 or a pharmaceutically acceptably salt thereof.

2. A compound of claim 1 wherein Q is a divalent oxygen atom.

3. A compound of one of claims 1 or 2 wherein n is the integer 1 or 2.

4. A compound of one of claims 1 or 2 wherein X is an oxygen atom and Z is an imino group.

5. A compound of one of claims 1 or 2 wherein n is the integer 1 or 2, and wherein X is an oxygen atom and Z is an imino group.

6. A method of treating heart failure in a patient in need thereof which comprises administering to the patient a cardiotonically effective amount of a compound of the structure:

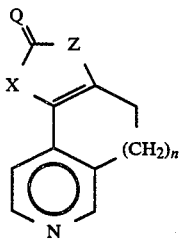

wherein
Q is a divalent sulfur or oxygen atom; one of X and Z is an oxygen atom and the other is an imino (NH) group; and n is 0 or the integer 1 or 2 or a pharmaceutically acceptably salt thereof.

7. A method of claim 6 wherein Q is a divalent oxygen atom.

8. A method of one of claims 6 or 7 wherein n is the integer 1 or 2.

9. A metod of one of claims 6 or 7, wherein X is an oxygen atom and Z is an imino group.

10. A method of enhancing myocardial contractile force in a patient in need thereof which comprises administering to the patient a compound of the structure:

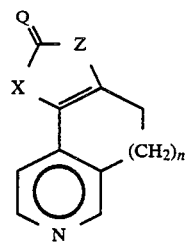

wherein Q is a divalent sulfur or oxygen atom; one of X and Z is an oxygen atom and the other is an imino (NH) group; and n is 0 or the integer 1 or 2 or a pharmaceutically acceptable salt thereof in an amount which effectuates an enhancement of myocardial contractile force.

11. A method of claim 10 wherein Q is a divalent oxygen atom.

12. A method of one of claims 10 or 12 wherein n is the integer 1 or 2.

13. A method of one of claims 10 or 12 wherein X is an oxygen atom and Z is an imino group.

14. A method of one of claims 6 or 7 wherein n is the integer 1 or 2, and wherein X is an oxygen atom and Z is an imino group.

15. A method of one of claims 10 or 11 wherein n is the integer 1 or 2, and wherein X is an oxygen and Z in an imino group.

16. A pharmaceutical composition useful in the treatment of heart failure comprising a compound of the structure:

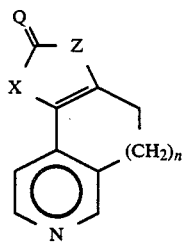

wherein
Q is a divalent sulfur or oxygen atom; one of X and Z is an oxygen atom and the other is an imino (NH) group; and n is 0 or the integer 1 or 2 or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 4,803,210
DATED : February 7, 1989
INVENTOR(S) : W.D. Jones; G.P. Claxton; R.A. Schnettler; R.C. Dage It is certified that error appears in the above-identified patent and that said Letters Patent is hereby corrected as shown below:

At Column 1, Line 55, the patent reads "intoxioation" and should read --intoxication--.

At Column 3, Line 40, the patent reads:

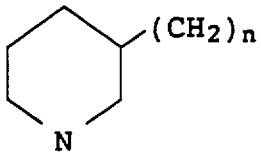

and should read:

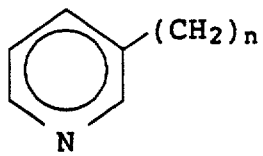

At Column 4, Line 6, the patent reads "discused" and should read --discussed--.

At Column 4, Line 10, the patent reads "Fundenmentals" and should read --Fundamentals--.

At Column 5, Line 1, the patent reads " genreally" and should read --generally--.

At Column 7, Line 17, the patent reads "2," and should read --2'--.

At Column 7, Line 18, the patent reads "3," and should read --3'--.

At Column 7, Line 56, the patent reads "3" and should read --3'--.

UNITED STATES PATENT AND TRADEMARK OFFICE
CERTIFICATE OF CORRECTION

PATENT NO. : 4,803,210

DATED : February 7, 1989

INVENTOR(S) : W.D. Jones; G.P. Claxton; R.A. Schnettler; R.C. Dage

It is certified that error appears in the above-identified patent and that said Letters Patent is hereby corrected as shown below:

At Column 7, Line 60, the patent reads "hyroxyimino" and should read --hydroxyimino--.

At Column 11, Line 36, the patent reads "as wells as" and should read ---as well as--.

At Column 12, Line 13, the patent reads "aded" and should read --added--.

At Column 14, Line 21, the patent reads "(500 ml), The" and should read --(500 ml). The--

At Column 16, Claim 15, the patent reads "and z in an imino" and should read --and z is an imino--.

Signed and Sealed this

Twenty-eighth Day of November 1989

*Attest:*

JEFFREY M. SAMUELS

*Attesting Officer*      *Acting Commissioner of Patents and Trademarks*